US00PP20767P3

(12) United States Plant Patent
Schuurman

(10) Patent No.: US PP20,767 P3
(45) Date of Patent: Feb. 23, 2010

(54) FLORIBUNDA ROSE NAMED 'SUNSTAR'

(50) Latin Name: *Rosa hybrida*
Varietal Denomination: Sunstar

(75) Inventor: Frank B. Schuurman, Whenuapai (NZ)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 12/216,893

(22) Filed: Jul. 11, 2008

(65) Prior Publication Data

US 2010/0011473 P1 Jan. 14, 2010

(51) Int. Cl.
*A01H 5/00* (2006.01)

(52) U.S. Cl. ..... Plt./146

(58) Field of Classification Search ..... Plt./146
See application file for complete search history.

(56) References Cited

OTHER PUBLICATIONS

Upov Plant Variety Database Jun. 2008 p. 1.*

* cited by examiner

*Primary Examiner*—Annette H Para
(74) *Attorney, Agent, or Firm*—Buchanan Ingersoll & Rooney PC

(57) ABSTRACT

A new and distinct variety of Floribunda rose plant is provided which abundantly forms on a nearly continuous basis attractive semi-double self-cleaning orange blossoms having petals that are yellow at the point of attachment. The plant exhibits a vigorous, compact, and substantially rounded growth habit. The attractive dark green glossy foliage contrasts nicely with the orange and yellow blossom coloration. Above average disease resistance is displayed particularly with respect to mildew (both powdery mildew and downy mildew) and rust. Also, a very short time between bloom cycles commonly is required. The new variety is particularly well suited for growing as attractive ornamentation in parks and gardens.

2 Drawing Sheets

Figure 1:
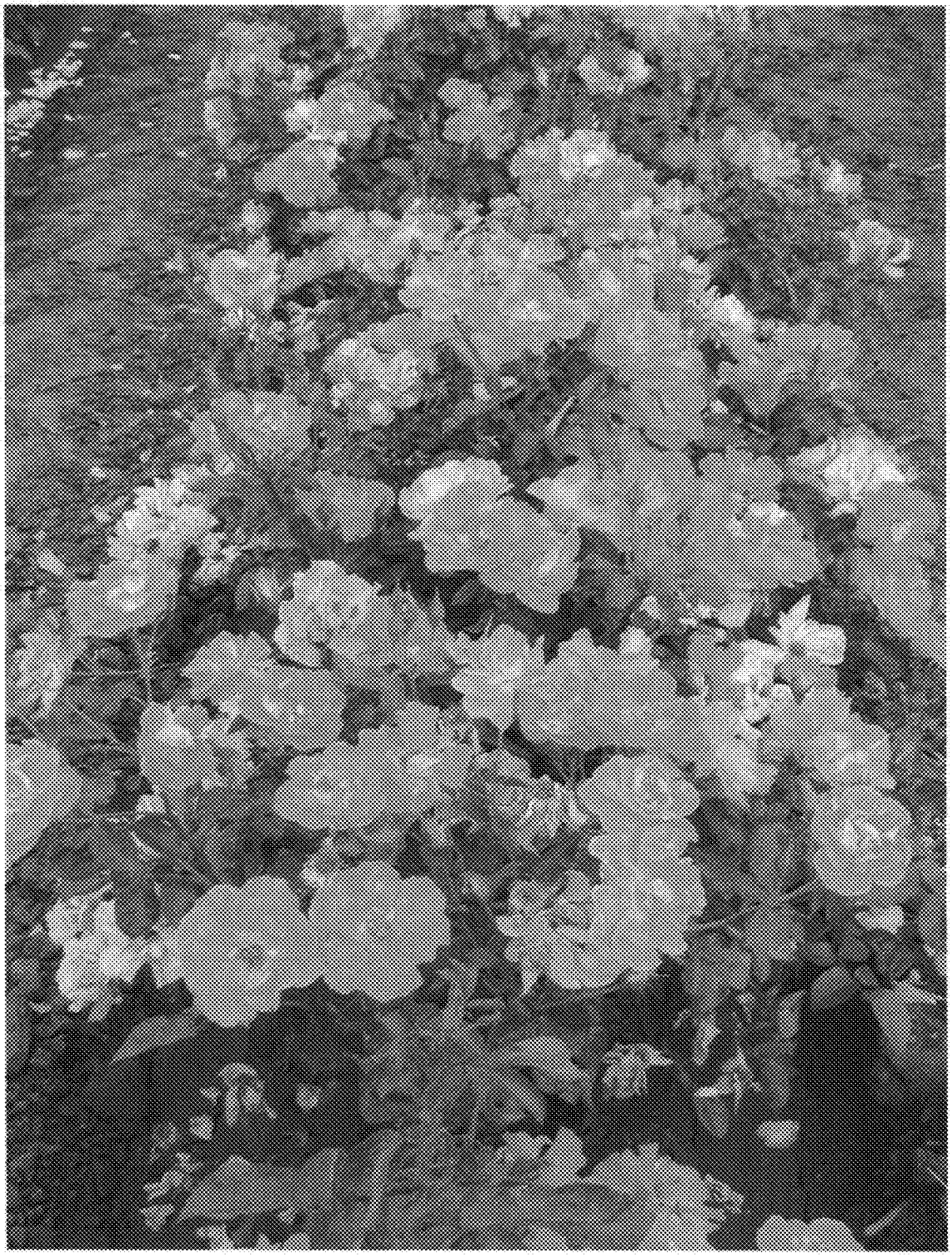

Botanical/commercial classification: *Rosa hybrida*/Floribunda Rose Plant.

Varietal denomination: cv. Sunstar.

SUMMARY OF THE INVENTION

The new variety of *Rosa hybrida* Floribunda rose plant was created by artificial pollination wherein two parents were crossed which previously had been studied in the hope that they would contribute the desired characteristics. The female parent (i.e., the seed parent) was the 'Alexander' variety (non-patented in the United States). The male parent (i.e., the pollen parent) was the 'Golden Emblem' variety (U.S. Plant Pat. No. 5,121). The parentage of the new variety can be summarized as follows:

'Alexander'×'Golden Emblem'.

The seeds resulting from the above pollination were sown and small plants were obtained which were physically and biologically different from each other. Selective study resulted in the identification of a single plant of the new variety.

It was found that the new Floribunda rose plant of the present invention:

(a) exhibits a vigorous, compact, and substantially rounded growth habit, (b) abundantly forms on a nearly continuous basis attractive semi-double self-cleaning orange blossoms having petals that are yellow at the point of attachment, (c) forms in abundance dark green foliage having a glossy aspect that contrasts well with the orange and yellow blossom coloration, (d) displays above average disease resistance particularly with respect to mildew and rust, and (e) is particularly well suited for growing as attractive ornamentation in parks and gardens.

A very short time between bloom cycles commonly is displayed. No hips have been formed during observations to date.

The new variety well meets the needs of the horticultural industry and can be grown to advantage in the landscape where attractive ornamentation is desired.

The new variety readily can be distinguished from its Hybrid Tea parental varieties. For instance, the 'Alexander' variety forms vermilion-red double blossoms possessing approximately 25 petals. The 'Golden Emblem' variety forms bright yellow blossoms. The new variety further can be readily distinguished from the 'Meimonblan' variety (U.S. Plant Pat. No. 12,579) upon an inspection of the blossoms. More specifically, the 'Meimonblan' variety forms tangerine orange blossoms that possess a greater number of petals.

The new variety has been found to undergo asexual propagation at Wasco, Calif., U.S.A., by budding. Such asexual propagation has shown that the characteristics of the new variety are stable and are strictly transmissible by such asexual propagation from one generation to another. Accordingly, the new variety can be asexually reproduced in a true-to-type manner.

The new variety has been named 'Sunstar', and is being marketed under the SPANISH SUNSET trademark.

BRIEF DESCRIPTION OF THE PHOTOGRAPHS

The accompanying photographs show as nearly true as it is reasonably possible to make the same, in color illustrations of this character, typical specimens and plant parts of the new variety. The rose plants of the new variety were approximately two years of age and were observed during October 2007 while budded on '*Dr. Huey*' understock (non-patented in the United States) and growing outdoors at Wasco, Calif., U.S.A.

Figure 2:
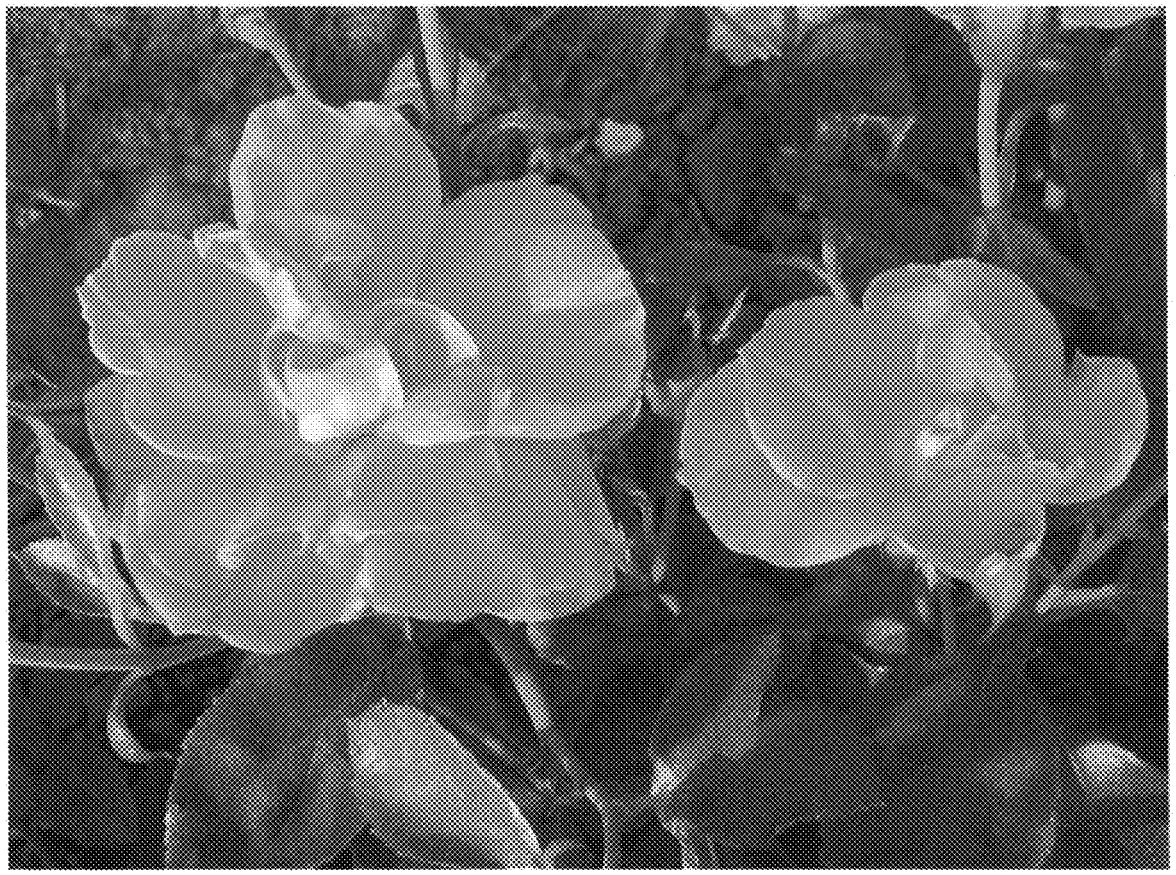

FIG. 1 — illustrates a row of typical flowering plants of the new variety wherein the blossoms are shown in various stages of development; and FIG. 2 — illustrates a close view of a pair of fully open blossoms of the new variety, as well as the appearance of typical dark green glossy leaves.

DETAILED DESCRIPTION

The chart used in the identification of the colors is that of The Royal Horticultural Society (R.H.S. Colour Chart), London, England. The description is based on the observation of two-year-old plants during June while budded on '*Dr. Huey*' understock and growing in containers near West Grove, Pa., U.S.A.

Class: Floribunda.

Plant:

*Height.*—Approximately 1.3 m on average at the end of the growing season.

*Width.*—Approximately 1.3 m on average at the end of the growing season.

*Habit.*—Vigorous, compact, and substantially rounded.

Branches:

*Color.*—Young stems: near Yellow-Green Group 144A. Adult wood: near Yellow-Green Group 146C.

*Thorns.*—commonly approximately 0.1 to 1.3 cm in length plus a very few smaller prickles, angled slightly downward with a moderately narrow base, and commonly year Yellow-Green Group 152D in coloration.

Leaves:

*Stipules.*—Commonly approximately 0.7 to 1.2 cm in length, moderately narrow in width, and possess medium-long points which commonly turn out at an angle more than 45 degrees.

*Petioles.*—Smooth in texture, commonly approximately 24 mm in length on average, approximately 2 mm in width on average, and near Yellow-Green Group 146C and 146D in coloration.

*Size.*—Commonly approximately 8 to 12 cm in length on average, and approximately 6 to 8 cm in width on average at the widest point.

*Leaflets.*—Number: 3, and 5 (most frequently). Arrangement: alternate and pinnately compound. Shape: typically ovate to elliptical with an acute to cuspidate apex and a generally obtuse base. Size: the terminal leaflets commonly are approximately 4 to 5 cm in length and approximately 3 to 4 cm in width on average. Serration: small and single (as illustrated). Texture: physically moderately thick. General appearance: compact, rather dense, dark green, and glossy. Venation: pinnate. Color (young foliage): upper surface: commonly between Green Group 137C and Yellow-Green Group 144A, and commonly suffused with Greyed-Purple Group 183A and Greyed-Purple Group 187A. under surface: commonly between Green Group 138B and Yellow-Green Group 144B, and commonly moderately suffused with Greyed-Purple Group 183B. Color (adult foliage): upper surface: commonly Green Group 137A. under surface: commonly Green Group 137C.

Inflorescence:

*Number of flowers.*—Commonly borne singly and sometimes two or more flowers on short to medium length stems.

*Peduncle.*—Smooth, commonly approximately 2.2 to 4.2 cm in length on average, average in caliper, commonly with a few stipulate glands and hairs, Yellow-Green Group 144A in coloration and sometimes moderately blushed on the side exposed to the sun with between Greyed-Red Group 178A and Greyed-Purple Group 183B in coloration.

*Sepals.*—Number: five. Texture: the inner surfaces commonly are covered with fine wooly tomentum, the margins commonly are lined with many stipulate glands and hairs, and sometimes 1 or 2 small slender foliaceous extensions are present. Color: near Yellow-Green Group 144C at the base and gradually changing to near Yellow-Green Group 144A at the apex. Configuration: Approximately 3 cm in length on average, and approximately 0.9 cm in width on average at the widest point.

*Buds.*—Shape: ovoid and very pointed. Length: approximately 1.7 to 2.5 cm on average as the calyx breaks. Width: approximately 1.2 to 1.6 cm on average at the widest point as the calyx breaks. Texture: commonly bear a few stipulate glands. Color: commonly between Green Group 137C and Yellow-Green Group 144A before the calyx breaks.

*Flower.*—Shape: semi-double, moderately high-centered when partially open, and flat to cup-shaped when fully open. Diameter: approximately 7 to 9 cm on average when fully open. Color (when newly opened): upper surface: near Orange-Red Group 33B with Yellow-Orange Group 15A at the point of attachment. under surface: near Red Group 39B suffused with Orange Group 29B and Yellow Group 12B at the point of attachment. Color (when fully open): near Red Group 51B, edged with Red Group 51A, and Yellow-Orange Group 18A at the point of attachment. Fragrance: none. Lasting quality: the blossoms commonly last approximately 4 to 5 days on average on the plant depending upon the environmental conditions that are encountered. Petal number: commonly approximately 10 to 12 on average under normal growing conditions. Petal shape: typically substantially round to broadly obovate commonly with substantially rounded apices. Petal length: commonly approximately 4.5 cm on average. Petal width: commonly approximately 4.3 cm on average. Petal texture: medium to thick in thickness, very satiny to somewhat velvety on the upper surface, and moderately shiny to satiny on the under surface. Petal arrangement: spiraled. Petal drop: the petals commonly detach cleanly. Stamen number: approximately 110 on average. Anthers: medium in size, regularly arranged around the styles, approximately 3.9 mm in length on average, 1.7 mm in width on average, all open at substantially the same time, and commonly near Yellow-Orange Group 19A to Yellow-Orange Group 20A in coloration. Pollen: present in a somewhat sparse quantity, and near Yellow-Orange Group 16C in coloration. Filaments: approximately 1 cm in length on average, and near Yellow-Orange Group 19A and Yellow-Orange Group 20A in coloration. Pistils: approximately 70 on average. Stigmas: near Yellow-Orange Group 18A in coloration. Styles: moderately short, somewhat uneven in height, relatively thin in caliper, tend to be bunched together, and near Red Group 49C and Yellow-Orange Group 18A in coloration. Ovaries: typically enclosed within the calyx. Hips: none observed to date.

Development:

*Vegetation.*—Very vigorous.

*Blooming.*—Abundant and nearly continuous.

*Resistance to diseases.*—Above average disease resistance particularly with respect to mildew (both powdery and downy mildew) and rust when compared to other commercial Floribunda rose varieties being grown near West Grove, Pa., U.S.A.

*Aptitude to bear fruit.*—None observed under the growing conditions near West Grove, Pa., U.S.A.

*Hardiness.*—Grows well in U.S.D.A. Hardiness Zone Nos. 6A to 9A. Further cold hardiness testing is being conducted.

The new 'Sunstar' variety has not been observed under all possible environmental conditions to date. Accordingly, it is possible that the phenotypic expression may vary somewhat with changes in light intensity and duration, cultural practices, and other environmental conditions.

I claim:

1. A new and distinct Floribunda rose plant characterized by the following combination of characteristics:

(a) exhibits a vigorous, compact, and substantially rounded growth habit, (b) abundantly forms on a nearly continuous basis attractive semi-double self-cleaning orange blossoms having petals that are yellow at the point of attachment, (c) forms in abundance dark green foliage having a glossy aspect that contrasts well with the orange and yellow blossom coloration, (d) displays above average disease resistance particularly with respect to powdery mildew, downy mildew, and rust, and (e) is particularly well suited for growing as attractive ornamentation in parks and gardens;

substantially as herein shown and described.

* * * * *